United States Patent
Cline et al.

(10) Patent No.: US 6,270,872 B1
(45) Date of Patent: Aug. 7, 2001

(54) PARYLENE COATED DEVICES WITH ADHESIVE

(75) Inventors: Mojgan Cline, Bartlett; Daniel B. Snyder, Memphis, both of TN (US)

(73) Assignee: Schering-Plough Healthcare Products, Inc., Kenilworth, NJ (US)

( * ) Notice: Subject to any disclaimer, the term of this patent is extended or adjusted under 35 U.S.C. 154(b) by 0 days.

(21) Appl. No.: 09/313,473

(22) Filed: May 17, 1999

Related U.S. Application Data

(60) Provisional application No. 60/086,004, filed on May 19, 1998.

(51) Int. Cl.[7] .................................................. B32B 7/00
(52) U.S. Cl. .................. 428/40.1; 36/35 R; 36/36 R; 36/71; 128/882; 428/41.3; 428/41.4; 428/41.5; 428/41.7
(58) Field of Search .................. 428/40.1, 41.3, 428/41.4, 41.5, 41.7; 36/35 R, 36 R, 71; 128/882

(56) References Cited

U.S. PATENT DOCUMENTS

| | | | |
|---|---|---|---|
| 5,075,174 | 12/1991 | Pyle | 428/447 |
| 5,137,780 | * 8/1992 | Nichols | 428/336 |
| 5,406,163 | * 4/1995 | Carson | 310/334 |

FOREIGN PATENT DOCUMENTS

| | | |
|---|---|---|
| 507183 A2 | 10/1992 | (EP) . |
| WO 95/17215 | 6/1995 | (WO) . |

* cited by examiner

Primary Examiner—Nasser Ahmad
(74) Attorney, Agent, or Firm—Robert J. Lipka

(57) ABSTRACT

A device comprising an article coated with paralyne wherein an adhesive is adhered to said parylene coating is claimed. The adhesive can be a pressure sensitive adhesive or a non-pressure sensitive adhesive. The device, which has improved stay-on time, can be useful for applications to the body, such as sheet padding, a finger pad, a corn pad, a callus pad, a blister pad, a heel pad or a toe pad.

14 Claims, 1 Drawing Sheet

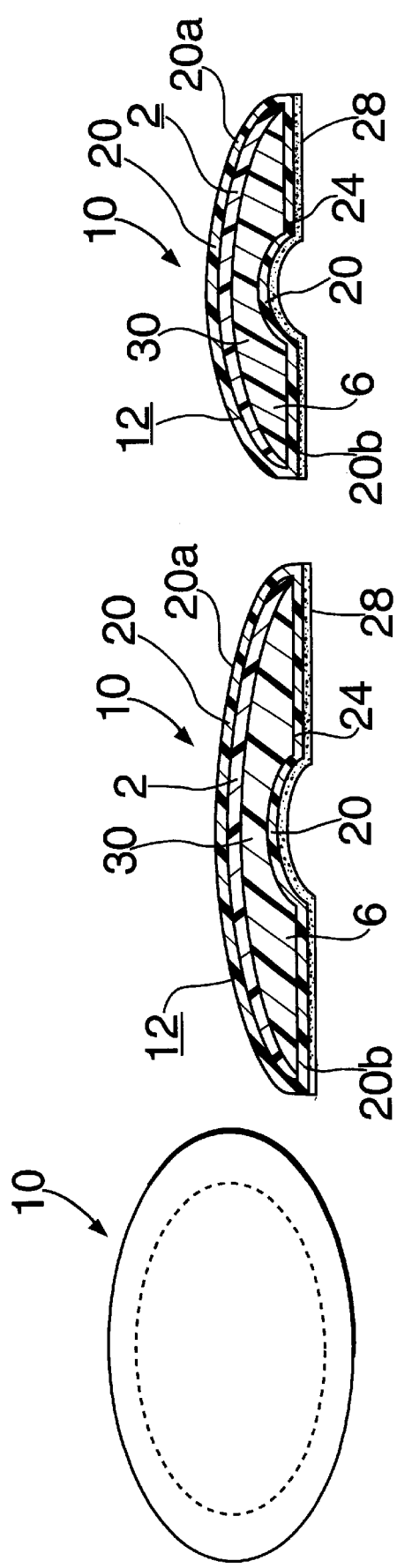

PARYLENE COATED DEVICES WITH ADHESIVE

This application claims benefit of Provisional Appln. Ser. No. 60/086,004 filed May 19, 1998.

BACKGROUND

Devices which are attached to the body and other surfaces for cushioning are known, for example, sheet padding, toe-crest pads, heel liners, elbow pads, knee pads, shin pads, forearm pads, wrist pads, finger pads, corn pads, callus pads, blister pads, bunion pads or toe pads. A problem with many of these devices is that they tend to become snagged or caught on clothing, socks, hosiery, bedsheets, shoes, carpeting and the like, and are inadvertently removed or torn away from the body or other surfaces where they were initially applied. It would be desirable to provide an device with improved "stay-on" time because inadvertent removal from the body or other surfaces is reduced or minimized.

SUMMARY OF THE INVENTION

Parylene is a coating which is characterized as having low-friction (i.e., slippery), chemically non-reactive, non-polar surface. It has been unexpectedly and surprisingly found that despite parylene's slippery, low friction properties, a device coated with parylene could still receive a pressure sensitive adhesive whose adhesion (i.e. bonding or achorage) to the parylene coating would be sufficiently strong that there is minimal delamination of the adhesive when the device is attached to a surface, such as the skin.

It has also been unexpected and surprisingly found that device of the present invention prepared with a parylene coating would have improved stay-on times, compared with comparable articles prepared without a parylene coating. For example, devices such as corn or callus pads prepared according to the present invention using the combination of parylene coating and pressure sensitive adhesive will have improved stay-one times compared with a comparable article prepared as described in PCT/US94/14164 (WO 95/17215).

It has also been unexpected and surprisingly found that a pressure sensitive adhesive can be adhered to certain articles even more securely by applying a parylene coating to at least a portion of the article before the adhesive is applied, to improve retention of the pressure sensitive adhesive on the article.

Accordingly, the present invention is directed towards a device comprising an article coated with parylene wherein a pressure sensitive adhesive is adhered to said parylene coating. Preferably, the parylene coating is continuous about the article. Optionally, the parylene coating may be discontinuous about the article. Preferably the article is comprised of an elastomer. Also preferred is that the pressure sensitive adhesive employed is an acrylic-based adhesive.

The pressure sensitive adhesive can have a peel strength of 0.33–4.93 kN/m (30–450 oz/in), a tack of 50–1000 grams or a shear strength of 10–10,000 minutes or greater.

In another embodiment, the present invention is directed towards a method for cushioning a limb, comprising contacting the limb with a device comprising a cushion or cushioning article coated with parylene wherein a pressure sensitive adhesive is adhered to said parylene coating.

BRIEF DESCRIPTION OF THE DRAWINGS

FIG. 1 is a perimeter view of corn pad 10.

FIG. 2 is a cross sectional side view of corn pad 10.

FIG. 3 is a cross sectional front view of corn pad 10.

FIG. 4 is a perimeter view of callus pad 40.

FIG. 5 is a cross sectional side view of a callus pad 40.

FIG. 6 is a cross-sectional front view of callus pad 40.

IN THE FIGURES

Referring to the drawings, device or corn pad 10 of FIGS. 1, 2 and 3 is comprised of an article 30, parylene coating 20 and pressure sensitive adhesive 28. In this embodiment, article 30 is comprised of exterior-facing topcover 2 bonded to a soft, cushioning layer 6. Parylene coating 20, which forms a continuous coating around article 30, including topcover 2 and cushioning layer 6, is comprised of an upper portion 20a and a lower portion 20b. Parylene upper portion 20a typically has a lower coefficient of friction than the upper surface 12 of topcover 2. Cushioning layer 6 can be of either uniform or non-uniform thickness, depending upon the application. Pressure sensitive adhesive 28 is bonded or anchored to parylene coating 20b, which coats the underside or lower surface 24 of cushioning layer 6.

Device or callus pad 40 of FIGS. 4, 5 and 6 is also comprised of an article 30, parylene coating 20 and pressure sensitive adhesive 28. In this embodiment, parylene coating 20, which forms a continuous coating or wrap around article 30, is comprised of an upper portion 20a and a lower portion 20b. In this embodiment, article 30 is comprised of only soft, cushioning layer 6. Upper portion 20a of parylene coating 20 typically has a lower coefficient of friction than the exterior surface of soft, cushioning layer 6. Pressure sensitive adhesive 28 is bonded or anchored to the parylene lower portion 20b, which coats the underside or lower surface 24 of cushioning layer 6.

DETAILED DESCRIPTION OF THE INVENTION

Devices

The term "device" refers to an article coated with parylene wherein a pressure sensitive adhesive is adhered to the parylene coating. The parylene coating on the article may be continuous (i.e., on all sides of the article) or discontinuous (i.e., with breaks or discontinuities in the coating). At a minimum, the pressure sensitive must be present on at least a portion of the parylene coating. Optionally and preferably, two opposing sides of the article are coated with the parylene: one parylene-coated side which receives the pressure sensitive adhesive and an exterior-facing, parylene coated side whose low-coefficient of friction helps improve the "stay-on" property of the device by minimizing clinging or snagging of the device. Preferably the device is entirely covered or coated with a parylene coating. A device of the present invention coated entirely or on opposing sides with parylene will have a low coefficient of friction (except where the pressure sensitive adhesive is applied), causing the article to easily slide or slip against another surface.

Preferably, the devices of the present invention have a softness that is measurable by a Shore 00 durometer, although devices with greater hardnesses, i.e., Shore A, may be employed. Determinations of the hardness of the parylene coated device can be made with any suitable durometer for testing hardness. One test method entails resting the edge of a Shore 00 or Shore A durometer on a material, applying a presser foot to the material without shock and taking the average of three readings. Further details for testing hardness can be found in ASTM Test Method D2240. One of ordinary skill in the art will appreciate that elastomers measured by the Shore 00 durometer scale are softer than those measured by the Shore A durometer scale. Preferably the parylene coated-device has a durometer of about 5 to 55 units (Shore 00), also from about 15 to about 45 units, more preferably from about 20 to about 35 units. It is desirable that devices of the present invention can cushion or protect the trunk or limb of the body against forces or shocks. For example, as a cushioning device the device may be sheet padding, a toe-crest pad, a heel liner, an elbow pad, a knee pad, a shin pad, a forearm pad, a wrist pad, a finger pad, a corn pad, a callus pad, a blister pad, a bunion pad or a toe pad. Limbs which can be protected with the present invention include legs, knees, shins, ankles, feet, toes, arms, elbows, forearms, wrists, hands, fingers or any part thereof.

Articles

The term "article" includes any item which can receive a parylene coating. Such articles typically have a higher surface coefficient of friction than the very smooth, lubricious or slippery surface provided by the parylene coating. The article may also contain mobile elements (such as oils, plasticers, plasticizers, solvents and the like) which could migrate or diffuse from the article without the parylene coating. The parylene coating can also prevent migration of such mobile elements from the article. Suitable articles can include elastomeric articles such as defined by Gessner G. Hawley, The Condensed Chemical Dictionary, 10th Edition, Van Nostrand Reinhold Co., New York, (1981), 1135 pages. The term "elastomer" as originally defined by Fisher (1940), refers to synthetic thermosetting high polymers having properties similar to those of vulcanized natural rubber, namely, the ability to be stretched to at least twice their original length and to retract very rapidly to approximately their original length when released. Among the better known elastomers are styrene rubbers, styrene-butadiene copolymers, polychloroprene (neoprene), nitrile rubber, butyl rubbers such as the non-halogenated rubbers, the chlorinated rubbers and brominated rubbers; polysulfide rubber ("Thiokol"), cis-1,4-polyisoprene, Krayton rubbers, ethylene-propylene terpolymers (EPDM rubber), polysiloxanes, silicone rubber and polyurethane rubbers and foams. A preferred class of polysiloxanes is described in U.S. Pat. No. 5,539,020, whose preparative teachings are incorporated herein by reference. Certain of these elastomers can be cross-linked with sulfur, peroxides or similar agents. Elastomers can also include uncross-linked polyolefins that are thermoplastic, generally known as TPO rubbers. Their extension and retraction properties are notably different from those of thermosetting elastomers, but they are well adapted to specific uses such as specialized mechanical products.

Also as defined by The Condensed Chemical Dictionary, above, the term "rubber" refers to any of a number of natural or synthetic high polymers having unique properties of deformation (elongation or yield under stress) and elastic recovery after vulcanization with sulfur or other cross-linking agent, which in effect changes the polymer from thermoplastic to thermosetting. Preferably the rubber is a synthetic high polymer. The yield or stretch of the vulcanized material ranges from a few hundred to over 1000 per cent. The deformation after break, called "permanent set" is usually taken as the index of recovery. It ranges from 5 to 10% for natural rubber to 50% or more for some synthetic elastomers, and varies considerably with the state of vulcanization and the pigment loading. Representative rubbers include nitrile rubbers or neoprene, GR-S rubbers, polyisoprene, polybutadienes, and polysiloxanes.

Articles employed in the present invention may also include foams such as acrylics and acrylates foams as well as polyurethane foams. The article may also include hydrocolloids or substances that yield a gel with water, such as colloidal suspensions. The article may also be comprised of metals such as aluminum, steel, iron, copper, tin or bronze.

The article may be of any convenient or desired shape. Preferably the article is shaped to be applied to the body trunk, including the back, rear, shoulders, chest or stomach; or to the limbs of the body, including legs, knees, shins, ankles, feet, toes, neck, head, arms, elbows, forearms, wrists, hands, fingers or any other part thereof. Also preferred is that the article is shaped or constructed as a cushion, to protect the body trunk or limbs against force or shock.

Parylene Coating

According to the pamphlet, "Parylene Conformal Coatings Specifications and Properties," by SCS Specialty Coating Systems Inc., 5707 West Minnesota Street, Indianapolis, Ind. (1992), 12 pages, Parylene is the generic name for members of a unique polymer series developed by the Union Carbide Corporation. Parylene polymers are deposited upon an article using vapor phase processes to form a transparent, colorless, slippery coating on the article to reduce surface friction. The parylenes resist room temperature chemical attack and are insoluble in all organic solvents up to 150° C. The parylenes are also unaffected by stress-cracking agents such as Hosptepal®, Igepal® and lemon oil. U.S. Pat. No. 5,075,174 describes an improved elastomeric gasket comprising a silicone elastomer coated with a parylene layer and teaches that the coating effectively alters the surface energy of the elastomeric materials so that airborne particles and fibers are no longer attracted thereto and that the coating is also effective in altering the adhesion properties of the elastomers in order to prevent the undesirable sticking of the gasket or seal on to metal equipment.

Specific examples of the parylenes which can be employed in the present invention include parylene N, which is poly-p-xylylene, parylene C, in which a chlorine atom has been substituted for one of the aromatic hydrogens, and parylene D which includes two chlorine atoms substituted on the aromatic group.

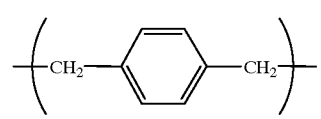

Parylene N

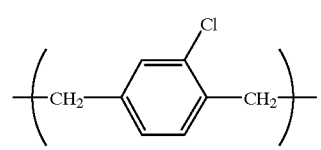

Parylene C

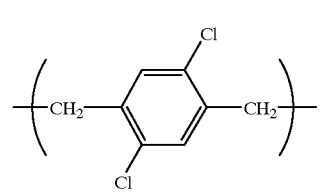

Parylene D

Parylene may be coated onto the article in a continuous coating or a discontinuous coating, so that only a portion of the article is coated.

Adhesives

The term "pressure sensitive adhesive" as used herein, refers to adhesives which, in dry form, are permanently tacky at room temperature and firmly adhere to surfaces upon mere contact, according to the Encyclopedia of Polymer Science and Engineering, Vol. 1, John Wiley & Sons, New York, (1985), p. 551. The pressure sensitive adhesive should be strong enough to hold the parylene coated cushioning device to the body trunk or limb, for about 8 hours to 48 hours or more. Also, it would be desirable that the pressure sensitive adhesive is adhered or bonded to the parylene coating on the article so there is minimal delamination of the adhesive from the article. Delamination refers to a failure mode where an adhesive splits away from an article to which it is bonded, because of its failure to adhere to the article. Generally the thickness of an adhesive applied to the polysiloxane elastomer can range from about one to about 20 mils (dry), preferably from about 2 to about 8 mils.

Pressure sensitive adhesives which can be employed for bonding to an the parylene coating can include, but are not limited to the following:

A. Solvent-based acrylic adhesives such as:
GMS 737, GMS 788 and GMS 2655, trademarks of Monsanto Corporation, St. Louis, Mo.;
National Starch Durotak 72-9720 and 80-1197, trademarks of National Starch & Chemical Corp., Bridgewater, N.J.
Ashland's AROSET 111 3-AD-40 and 1085-Z-45, trademark of Ashland Oil Co., Ashland, Ky.

B. Solvent-based rubber adhesives such as:
National Starch 36-6172
Hauthaway 59-133, trademark of C.L. Hauthaway, Lynn, Mass.

C. Acrylic emulsion based adhesives such as:
Monsanto GME 2397 and GME 3011;
Rohm & Haas N580 and N619, trademark of Rohm & Haas Co., Philadelphia, Pa.
Unocal 76 RES 9646, trademark of Unocal Corp., Los Angeles, Calif.;
Ashland's AROSET 2022-W-50

D. Adhesive Transfer Tapes such as:
3M F-9465 PC, trademark of 3M Co., St. Paul, Minn.
Avery-Denison MED 1116, trademark of Avery Dennison Corp., Pasedena, Calif.
ARCare 7530, trademark of Adhesive Research Inc., Glen Rock, Pa.; and
RX230U, trademark of Coating Science Inc., Bloomfield, Conn.;

E. Synthetic Rubber Hot-Melt Based Pressure Sensitive Adhesives
National Starch 34-4144
Swift 40-11, trademark of Swift Adhesives Inc.

F. Silicone-Based Pressure Sensitive Adhesives
GE 6475 and SCA 1000, trademarks of the General Electric Company;
Dow Corning Q2-7736, trademark of Dow-Corning Corp., Midland, Mich.

Preferably the pressure sensitive adhesive is a sovent-based rubber, an acrylic adhesive, or a silicone-based adhesive.

A tackifier is any substance which enhances the property of tack of a pressure sensitive adhesive. Suitable tackifiers include rosin acid derivatives such as Pentalyn H of the Hercules Corporation, terpene based derivatives and synthetic C-5 tackifiers such as Escorez 1310 of the Exxon Corporation. The amount of tackifier in the adhesive can range from about 1 to about 60% by weight of the adhesive, preferably from about 5 to about 40%.

Quantitative measurements of tackiness for the pressure sensitive adhesive can be made using a suitable tack tester, such as a Polyken® probe tack tester, a rolling ball tack tester, a peel tester or combinations thereof. Tack can be tested with the Polyken® probe tester in accordance with any suitable procedure, such as American Society For Testing and Materials (ASTM) Designation: D2979-71 (Reapproved 1982), Standard Test Method for Pressure-Sensitive Tack of Adhesives Using an Inverted Probe Machine, pp. 187–189, from the Annual Book of ASTM Standards, Vol.15.09. The Polyken® probe tack tester is the trademark of the Kendall Company, under license by Testing Machines Inc., Mineola, Long Island, N.Y. Using a a Polyken® probe tack tester, the pressure sensitive adhesive can have a tack of about 50 to about 1000 grams, preferably from about 100 to about 600 grams, wherein the polyken probe tack tester is set at a dwell time of one second and a speed of one centimeter per second. The tack of the adhesive can also be tested with a rolling ball tack tester in accordance with Pressure Sensitive Tape Council, Test Methods for Pressure Sensitive Tapes, 10th Edition, PSTC-6, revised August, 1989, pp. 33–34 or ASTM D3121. Tack can also be tested with a peel tester in accordance with Pressure Sensitive Tape Council, Test Methods for Pressure Sensitive Tapes, 10th Edition, PSTC-1, revised August 1989, pp. 23–24. Using a peel tester, the pressure sensitive adhesive can have a peel strength of about 30 to about 450 ounces per inch (oz/in) (0.33–4.93 kN/m), preferably from about 125 to about 300 oz/in (1.37–3.28 kN/m). The shear strength of the adhesive can range from about 10 to about 10,000 minutes or more, preferably from about 10 to about 3000 minutes, more preferably from about 25 to about 800 minutes.

Alternatively, non-pressure sensitive adhesives can be employed, i.e., an adhesive which is directly applied to the parylene coating on the article as a liquid or "wet" so that an article coated with parylene, which has received the wet or liquid, non-pressure sensitive adhesive is directed adhered to another surface, i.e. polymer substrate. In this case, the adhesive lacks the tack described for the pressure sensitive adhesives, above. As the non-pressure sensitive adhesive dries, an adhesive bond is formed between the parylene coated article and the other surface, i.e. heel cup. Examples of non-pressure sensitive adhesives include the cyanoacrylates, epoxies and certain hot-melt adhesive formulations which lack tackiness upon cooling.

Device Preparation & Use

The device of the present invention can be prepared by coating an article with parylene followed by application of the pressure sensitive adhesive to the parylene-coated article. Typically, the pressure sensitive adhesive is laminated onto the parylene-coated article. Lamination refers to the process by which a pressure sensitive adhesive is applied onto a parylene coated article, prior to which the pressure sensitive adhesive is precoated onto a backing or release liner, before the adhesive is adhered or bonded to the parylene coated article. Optionally, the contact or application of the pressure sensitive adhesive onto the parylene-coated article may be performed under pressure using an apparatus such as a roller or a stamp.

Alternatively, the parylene-coated article may be pre-treated with a modifier such as a low temperature gaseous plasma for a time effective to modify the surface of the parylene, prior to bonding the pressure sensitive adhesive to the pre-treated parylene surface. The low temperature plasma can use any convenient gas, such as argon, nitrous oxide, oxygen, purfied air, carbon dioxide, hydrogen or mixtures thereof.

Several physical and chemical tests can be performed to evaluate the effect that different gaseous plasmas have on modifying the surface of a parylene surface for bonding or anchoring a pressure sensitive adhesive. These tests include X-ray photoelectron spectroscopy (XPS) also known as electron spectroscopy for chemical analysis (ESCA), attenuated total reflectance fourier transform infrared spectroscopy (ATR-FTIR) analysis, surface energy determinations (contact angle/dyne pens), 180° peel test, shear strength test, polyken probe tack test (adhesive), aging studies and evaluation of adhesive failure mode such as delamination. For example, application of the adhesive to the parylene coated article, the 180° peel test, shear strength test, polyken Probe Tack test can be used to monitor the bondability of the adhesive with the surface of the parylene coated article through the use of accelerated aging studies. The 180° peel test can be performed as described in Pressure Sensitive Tape Council, Test Methods for Pressure Sensitive Tapes, 10th Edition, PSTC-1, revised August 1989, pp. 23–24. The shear test can be performed as described in PSTC-7, Pressure Sensitive Tape Council, Test Methods for Pressure Sensitive Tapes, 10th Edition, revised August 1989, pp. 35–37. Such methods can be slightly modified as needed. For example, instead of a pressure sensitive tape, the adhesive can be applied, prior to testing, to a substrate such as a elastomer, sheet or plaque. Preferably, a suitable release liner is placed over the pressure sensitive adhesive on the parylene coated device to prevent contamination of the adhesive prior to its contact with the skin or other surfaces. Typical release liners include silicone-coated polymers of the following: high density polyethylene (HDPE), polyester (ie. Mylar®) and polyethylene terephthalate (PET).

The device of the present invention, i.e. an article coated with parylene wherein a pressure sensitive adhesive is adhered to said parylene coating, may conveniently used by removing or peeling away the release liner and attaching the device to any desired surface, such as skin, the interior of a shoe surface, and the like.

Preparation of Starting Materials

Preparative Example

Preparation of Parylene Coated Article

Using a technique known as compression molding, a mold cavity heated to a conventional vapor deposition system having serially, a vaporizer, a pyrolysis unit or furnace and a vapor deposition chamber is used to deposit a coating of 2-chloro-p-xylylene (Parylene C), poly-p-xylylene (Parylene N), or 2, 4-dichloro-p-xylylene (Parylene D) onto an elastomeric article made of a polysiloxane polymer. An untreated elastomeric article is placed in the vapor deposition chamber. In the vaporizer, a quantity of p-xylylene is evaporated at 150° C. and approximately 1 torr. The p-xylylene vapors travel to the pyrolysis unit or furnace where they are then heated in the furnace at least 680° C. and 0.5 torr to pyrolize the p-xylylene dimer and form the corresponding monomeric diradical, para-xylylene. The monomer diradical then enters the deposition chamber at ambient temperatures (about 25° C.) and about 0.1 torr, where it condenses on the surface of the article to form a polymer or parylene coating which is continuous about all sides of the article.

EXAMPLES

The present examples are provided to illustrate typical devices of the present invention, but the scope of the invention is not to be considered limited to the specific examples given.

Example 1.

Device prepared by laminating a solvent-based acrylic pressure sensitive adhesive to the surface of a parylene-coated article. A parylene coated article prepared as in the Preparative Example is laminated with an acrylic pressure sensitive adhesive by contacting the parylene coated article with a release liner containing Monsanto GMS 737, a solvent based adhesive.

Example 2.

Device prepared by laminating a solvent-based rubber pressure sensitive adhesive to the surface of a parylene-coated article. A parylene-coated article prepared as in the Preparative Example is laminated with a solvent-based pressure sensitive adhesive by using a pressure roller to contact the parylene coated article with a release liner containing National Starch 36-6172, a solvent based rubber adhesive.

Example 3.

Device prepared by laminating an acrylic emulsion pressure sensitive adhesive to the surface of a parylene-coated article. A parylene-coated article prepared as in the Preparative Example is laminated with an acrylic emulsion based pressure sensitive adhesive by contacting the parylene-coated article with a release liner containing Ashland Aroset 2022-W-50, an acrylic emulsion pressure sensitive adhesive.

Example 4.

Device prepared by laminating an adhesive transfer tapes to the surface of a parylene-coated article.

A parylene-coated article prepared as in the Preparative Example is laminated with a 3M F-9465 PC, trademark of 3M Co. St. Paul, Minn., a double coated polyester tape in which the polyester tape is coated on both sides with a pressure sensitive adhesive.

Example 5.

Device prepared by laminating a synthetic rubber hot-melt pressure sensitive adhesive to the surface of a parylene coated article.

A parylene-coated article is prepared as in the Preparative Example. A release liner is precoated with National Starch 34-4144, a synthetic rubber hot-melt adhesive pressure sensitive adhesive, which is spread uniformly over the surface of the release liner. The hot-melt adhesive is then laminated onto the parylene coated article by contact application with the article.

Example 6.

Device prepared by laminating a silicone pressure sensitive adhesive to the surface of a parylene-coated article A parylene-coated article prepared in the Preparative Example is laminated with GE6475, a silicone-based pressure sensitive adhesive.

Example 7.

Heel cup device with cushion insert using a non-pressure sensitive adhesive.

A molded rubber heel cup is prepared with a recess or central cut-out in the heel bottom for receiving a polyurethane cushion insert or article having approximately the shape of a rectangular solid. Only one side of the polyurethane cushion is coated (i.e. the parylene coating is discontinuous on the article) with parylene C as described in the Preparative Example. Using a pen applicator, a bead of cyanoacrylate (Loctite Corporation), a non-pressure sensitive adhesive) is applied to the parylene coated side of the polyurethane cushion and the cushion is bonded or adhered to the heel cup recess for improved stay-on.

Example 8.

Corn pad with improved stay-on time.

A first group of corn pads ("the control corn pads") having a polysiloxane topcover, polysiloxane cushioning layer and a pressure sensitive adhesive adhered directly to the cushioning layer is prepared according to the procedures in PCT/US94/14164 (WO 95/17215). A second group of corn pads ("the parylene coated corn pads") is prepared by coating the polysiloxane topcover and polysiloxane cushioning layer with a coating of Parylene-C, followed by application of Monsanto 2875, an acrylic-based pressure sensitive adhesive to the parylene coating on the underside or lower surface of the cushioning layer. A wear test was conducted in which male and female subjects wore samples of the control corn pads and parylene coated samples that were placed according to a randomization schedule on the toes of both feet for 48 hours. The results of the wear test are provided in the table below.

| Control Corn Pads | Parylene Coated Corn Pads | % Improvement in Stay-On Time |
|---|---|---|
| % Stay On | | |
| 35 | 45 | 29% |

In this wear test, the Parylene coated corn pads outperformed the corresponding control corn pads by 29% after 48 hours. This means that after 48 hours, there were 29% more parylene-coated corn pads than control corn pads on the subjects' toes.

Example 9.

Corn pad with improved stay-on time

Essentially the same procedure was followed as in Example 8, except that a different acrylic adhesive (i.e., tackified Monsanto 737) was used as the pressure sensitive adhesive and two wear tests were conducted. The results of two wear tests are presented in the table below.

| Wear Test | Control Corn Pads | Parylene Coated Corn Pads | % Improvement in Stay-On Time |
|---|---|---|---|
| | % Stay On | | |
| No. 1 | 48 | 75 | 56% |
| No. 2 | 32 | 50 | 56% |

In both Wear Tests Nos. 1 and 2, the Parylene coated corn pads outperformed the corresponding control corn pads by 56% after 48 hours. This means that after 48 hours, there were 56% more parylene-coated corn pads than control corn pads on the subjects' toes.

Example 10.

Corn pad with improved stay-on time

Essentially the same procedure was followed as in Example 8, except that GE 6574, a silicone-based adhesive was used as the pressure sensitive adhesive. The results of the wear test are provided in the table below.

| Control Corn Pads | Parylene Coated Corn Pads | % Improvement in Stay-On Time |
|---|---|---|
| % Stay On | | |
| 35 | 77 | 120% |

In this wear test, the parylene coated corn pads outperformed the corresponding control corn pads by 120% after 48 hours. This means that after 48 hours, there were 120% more parylene-coated corn pads than control corn pads on the subjects' toes.

We claim:

1. A cushioning device comprising an article coated with parylene wherein an adhesive is adhered to said parylene coatings and wherein the cushioning device is adapted to adhere to a human body.

2. The device of claim 1 wherein the adhesive is a pressure-sensitive adhesive.

3. The device of claim 1 wherein the parylene coating is continuous about said article.

4. The device of claim 1 wherein the parylene coating is discontinuous about said article.

5. The device of claim 1 wherein said parylene is parylene C, parylene N, parylene D or mixtures thereof.

6. The device of claim 1 wherein said parylene is parylene C.

7. The device of claim 1 wherein the thickness of said parylene coating on said article is in the range from about 0.3 to about 5 microns.

8. The device of claim 1 wherein the article is an elastomer.

9. The device of claim 8 wherein a topcover is bonded to said elastomer.

10. The device of claim 8 wherein the elastomer is a polysiloxane polymer.

11. The device of claim 9 wherein the elastomer is a polysiloxane polymer and the topcover is a polysiloxane polymer.

12. The device of claim 2 wherein the pressure sensitive adhesive has peel strength of 30-450 (oz/in), a tack of 50-1000 grams or a shear strength of 10–10,000 minutes.

13. The device of claim 2 wherein the pressure sensitive adhesive is a solvent-based rubber adhesive, an acrylic-based adhesive or a silicone-based adhesive.

14. The device of claim 2 which is sheet padding, a finger pad, a corn pad, a callus pad, a blister pad, a heel pad or a toe pad.

* * * * *